United States Patent [19]

Petersen et al.

[11] Patent Number: 4,547,503

[45] Date of Patent: Oct. 15, 1985

[54] 1-CYCLOPROPYL-6-FLUORO-1,4-DIHYDRO-4-OXO-7-[4-(OXO-ALKYL)-1-PIPERAZINYL]QUINOLINE-3-CARBOXYLIC ACIDS AND THEIR DERIVATIVES, AND ANTIBACTERIAL AGENTS CONTAINING THEM

[75] Inventors: Uwe Petersen, Leverkusen; Klaus Grohe, Odenthal; Hans-Joachim Zeiler, Velbert; Karl G. Metzger, Wuppertal, all of Fed. Rep. of Germany

[73] Assignee: Bayer Aktiengesellschaft, Leverkusen, Fed. Rep. of Germany

[21] Appl. No.: 560,026

[22] Filed: Dec. 9, 1983

[30] Foreign Application Priority Data

Dec. 29, 1982 [DE] Fed. Rep. of Germany ....... 3248505

[51] Int. Cl.[4] .................. A61K 31/495; C07D 401/04
[52] U.S. Cl. .................................. 514/254; 544/363; 546/156
[58] Field of Search ..................... 544/363; 424/250

[56] References Cited

U.S. PATENT DOCUMENTS 3,149,104 9/1961 Lesher et al. ..................... 544/362

OTHER PUBLICATIONS

Takase et al., "Chemical Abstracts," vol. 93, 1980, col. 93:168301t.
Takase et al., "Chemical Abstracts," vol. 93, 1980, col. 93:168305x.

Primary Examiner—Richard L. Raymond
Assistant Examiner—James H. Turnipseed
Attorney, Agent, or Firm—Sprung, Horn, Kramer & Woods

[57] ABSTRACT

The invention relates to 1-cyclopropyl-6-fluoro-1,4 dihydro-4-oxo-7-[4-(oxo-(alkyl)-1-piperazinyl]-quinoline-3-carboxylic acids of Formula (I), processes for their manufacture, compositions containing them and use of said compounds and compositions as antibacterial and/or feedstuff additives.

17 Claims, No Drawings

1-CYCLOPROPYL-6-FLUORO-1,4-DIHYDRO-4-OXO-7-[4-(OXO-ALKYL)-1-PIPERAZINYL]QUINOLINE-3-CARBOXYLIC ACIDS AND THEIR DERIVATIVES, AND ANTIBACTERIAL AGENTS CONTAINING THEM

The present invention relates to new 1-cyclopropyl-6-fluoro-1,4-dihydro-4-oxo-7-[4-(oxoalkyl)-1-piperazinyl]quinoline-3-carboxylic acids and their derivatives, processes for their preparation and antibacterial agents and feedstuffs additives containing them.

It has already been disclosed that 1-ethyl-6-fluoro-1,4-dihydro-4-oxo-7-(1-piperazinyl)quinoline-3-carboxylic acid (Norfloxacin) has antibacterial properties [J. Med. Chem. 23, 1358 (1980), U.S. Pat. No. 4,146,719].

It has now been found that the new 1-cyclopropyl-6-fluoro-1,4-dihydro-4-oxo-7-[4-(oxoalkyl)-1-piperazinyl]quinoline-3-carboxylic acids of the formula (I)

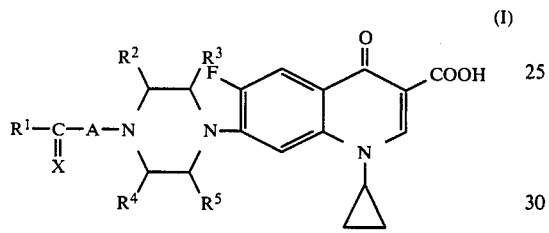

in which

R$^1$ denotes hydrogen, straight-chain or branched alkyl having 1 to 4 carbon atoms and phenyl which is optionally substituted 1-3 times by trifluoromethyl, methyl, ethyl, fluorine, chlorine, bromine, phenyl, hydroxyl or alkoxy having 1-4 carbon atoms, R$^2$, R$^3$, R$^4$ and R$^5$ can be identical or different and denote hydrogen, methyl, ethyl, n- or i-propyl, X denotes =O, =N—O—R′, =N—NH—R″ and =(OR‴)$_2$, in which R′ represents hydrogen, straight-chain or branched alkyl having 1 to 6 carbon atoms, cycloalkyl having 5 to 6 carbon atoms, chlorobenzy. or tetrahydropyranyl, R″ represents methyl, phenyl, carbamoyl or thiocarbamoyl and R‴ represents methyl and ethyl or (OR‴)$_2$ represents

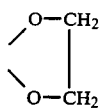

and

A denotes an alkylene group having 1-4 carbon atoms, which is optionally substituted by alkyl having 1-4 carbon atoms or phenyl, and their pharmaceutically utilisable acid addition, alkali metal and alkaline earth metal salts and hydrates, have a high antibacterial activity.

Those compounds of the formula I are preferred in which

R$^1$ denotes hydrogen, straight-chain or branched alkyl having 1-3 carbon atoms or phenyl which is optionally substituted 1-3 times by trifluoromethyl, methyl, ethyl, fluorine, chlorine, bromine, phenyl, hydroxyl or alkoxy having 1-4 carbon atoms, R$^2$, R$^3$, R$^4$ and R$^5$ denote hydrogen, methyl or ethyl, X denotes =O, =N—O—R′, =N—NH—R″ or =(OR‴)$_2$, in which R′ denotes hydrogen, alkyl having 1-4 carbon atoms, benzyl or tetrahydropyranyl, R″ denotes carbamoyl or thiocarbamoyl, R‴ denotes methyl or ethyl and A denotes alkylene having 1 to 3 carbon atoms, and their pharmaceutically utilisable acid addition, alkali metal and alkaline earth metal salts and hydrates.

Those compounds of the formula I are particularly preferred in which

R$^1$ denotes hydrogen, alkyl having 1-2 carbon atoms or phenyl which is optionally substituted 1-2 times by trifluoromethyl, methyl, fluorine, chlorine, hydroxyl or alkoxy having 1-2 carbon atoms, R$^2$ denotes hydrogen, methyl or ethyl, R$^3$ denotes hydrogen, R$^4$ denotes hydrogen, ethyl or methyl, R$^5$ denotes hydrogen or methyl, X denotes =O, =N—O—R′, =N—NH—R″ or =(OR‴)$_2$, in which R′ denotes hydrogen, alkyl having 1-2 carbon atoms, benzyl or tetrahydropyranyl, R″ denotes carbamoyl or thiocarbamoyl, R‴denotes methyl or ethyl and A denotes alkylene having 1-2 carbon atoms, and their pharmaceutically utilisable acid addition, alkali metal and alkaline earth metal salts and hydrates.

In addition, it has been found that the compounds of the formula (I) according to the invention are obtained when a compound of the formula (II)

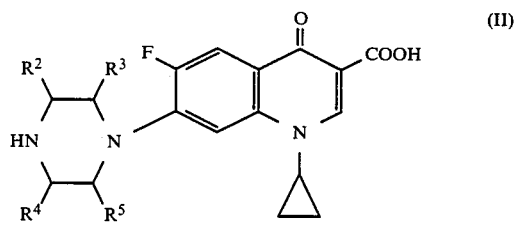

in which

R$^2$, R$^3$, R$^4$ and R$^5$ have the meaning indicated above, is reacted with a compound of the formula (III)

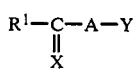

in which

R$^1$, X and A have the meaning indicated above and

Y represents halogen, preferably chlorine or bromine (method A).

The compounds according to the invention can also be obtained by reacting compounds of the formula (II)

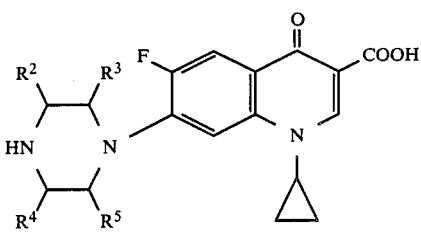

with alkenones of the formula (IV)

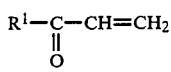

in which R¹ has the meaning indicated above,
to give the compounds of the formula (Ia)=(I; with X=O, A=—CH₂CH₂—) according to the invention (method B).

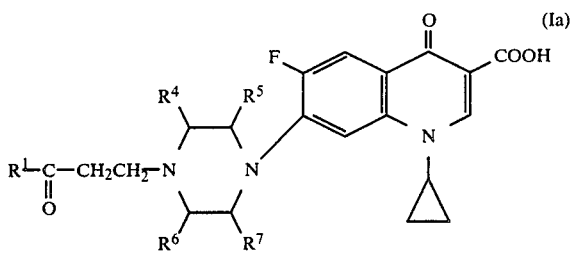

Moreover, the compounds according to the invention can be obtained by condensing compounds of the formula (V)

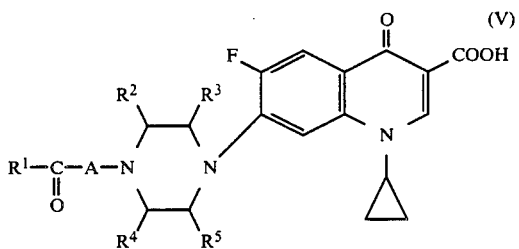

in which R¹, R², R³, R⁴, R⁵ and A have the meanings indicated above,
with compounds of the formula (VIa) or (VIb)

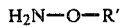       (VIa)

       (VIb)

in which R' and R'' have the meanings indicated above,
to give the compounds of the formula (Ib) (I; with X=N—O—R') or (Ic) (I; with X=NH—R'') respectively (method C).

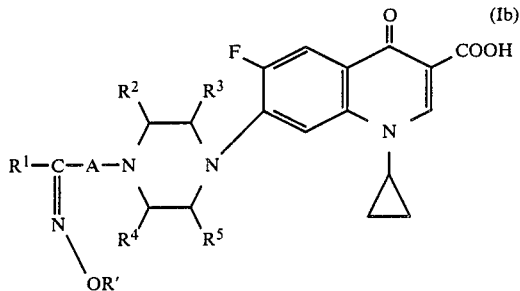

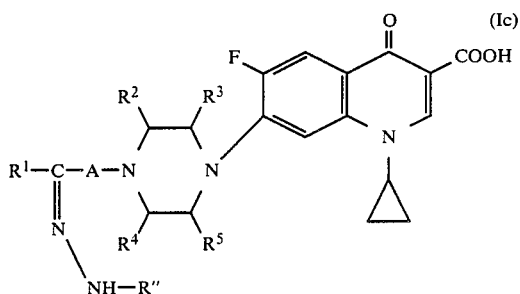

In this condensation, the compounds (VIa) and (VIb) can also be employed in the form of the hydrochlorides or sulphates.

Surprisingly, the 1-cyclopropyl-6-fluoro-1,4-dihydro-4-oxo-7-[4-(oxoalkyl)-1-piperazinyl]quinoline-3-carboxylic acids and their derivatives exhibit a considerably higher antibacterial activity than 1-ethyl-6-fluoro-1,4-dihydro-4-oxo-7-(1-piperazinyl)quinoline-3-carboxylic acid known from J. Med. Chem. 23, 1358 (1980) and U.S. Pat. No. 4,146,719. Thus they are suitable as active compounds in medicine; veterinary medicine in this context including the treatment of fish.

Thus the substances according to the invention represent an enrichment of pharmacy.

When, for example, in the reaction of (II) with (III) by method A, 1-cyclopropyl-6-fluoro-1,4-dihydro-4-oxo-7-(1-piperazinyl)quinoline-3-carboxylic acid and chloroacetone are used as the starting compounds, the course of the reaction can be represented by the following diagram:

CH₃—CO—CH₂—Cl +

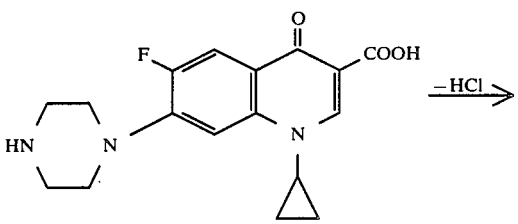

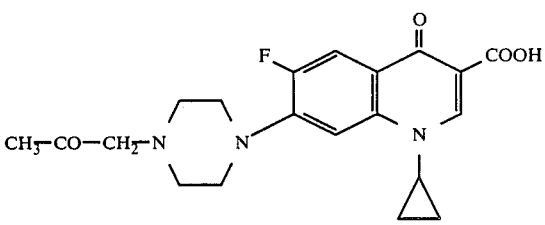

When, for example, in the reaction of (II) with (IV) by method B, 1-cyclopropyl-6-fluoro-1,4-dihydro-4-oxo-7-(1-piperazinyl)quinoline-3-carboxylic acid and methyl vinyl ketone are used as the starting substances, the course of the reaction can be represented by the following diagram:

CH₃—CO—CH=CH₂ +

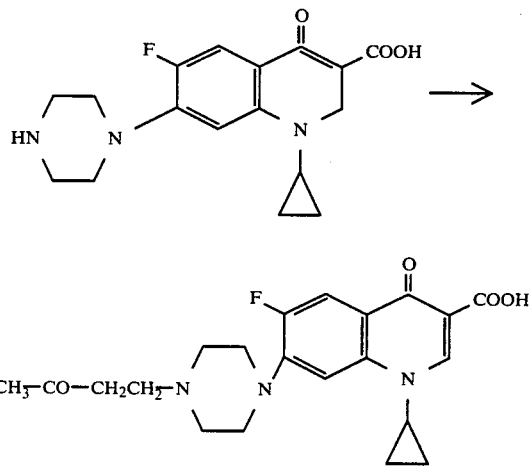

When, for example, in the reaction of (V) with (VI) by method C, 1-cyclopropyl-6-fluoro-1,4-dihydro-4-oxo-7-[4-(2-oxopropyl)-1-piperazinyl]quinoline-3-carboxylic acid and methoxyamine hydrochloride are used as the starting compounds, the course of the reaction can be represented by the following diagram:

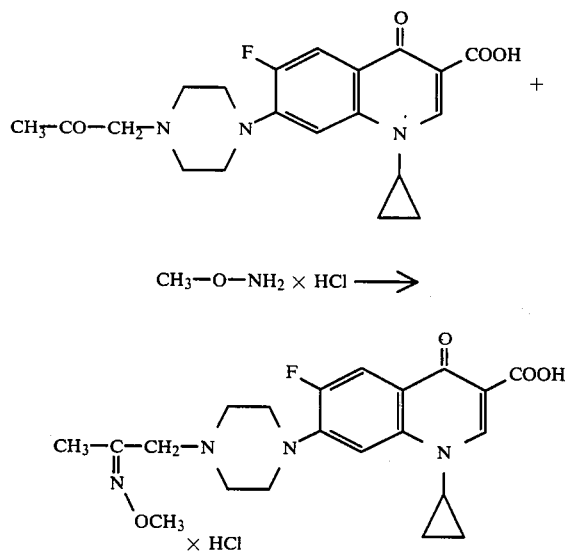

The 1-cyclopropyl-6-fluoro-1,4-dihydro-4-oxo-7-(1-piperazinyl)quinoline-3-carboxylic acids of the formula (II) used as starting compounds can be prepared by reaction of 7-chloro-1-cyclopropyl-6-fluoro-1,4-dihydro-4-oxoquinoline-3-carboxylic acid of the formula (VII)

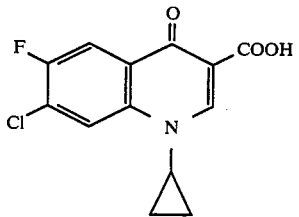

with piperazine or piperazine derivatives of the formula (VIII)

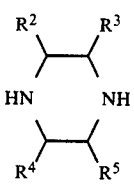

in which $R^2$, $R^3$, $R^4$ and $R^5$ have the meaning indicated above.

This reaction is carried out in a diluent, such as dimethyl sulphoxide, hexamethylphosphoric triamide, sulpholane, water, an alcohol or pyridine at temperatures of 20° C.–200° C., preferably at 80° C.–180° C. In carrying out the process, 1–15 mols of compound VIII, preferably 1–6 mols of compound VIII, are employed for 1 mol of carboxylic acid VII. When using equivalent amounts of the carboxylic acid VII and the piperazine derivative VIII, the reaction is carried out in the presence of an acid-binding agent, for example triethylamine, 1,4-diazabicyclo[2.2.2]octane or 1,8-diazabicyclo[5.4.0]undec-7-ene.

The following may be mentioned as examples of the starting materials of the formula (II) which can be prepared in this manner: 1-Cyclopropyl-6-fluoro-1,4-dihydro-4-oxo-7-(1-piperazinyl)quinoline-3-carboxylic acid, 1-cyclopropyl-6-fluoro-1,4-dihydro-4-oxo-7-(2,5-dimethyl-1-piperazinyl)quinoline-3-carboxylic acid, 1-Cyclopropyl-6-fluoro-1,4-dihydro-4-oxo-7-(3,5-dimethyl-1-piperazinyl)quinoline-3-carboxylic acid, 1-cyclopropyl-6-fluoro-1,4-dihydro-4-oxo-7-(3-methyl-1-piperazinyl)quinoline-3-carboxylic acid, 1-cyclopropyl-6-fluoro-1,4-dihydro-4-oxo-7-(3-ethyl-1-piperazinyl)-quinoline-3-carboxylic acid, 1-cyclopropyl-6-fluoro-1,4-dihydro-4-oxo-7-(3,5-diethyl-1-piperazinyl)quinoline-3-carboxylic acid, 1-cyclopropyl-6-fluoro-1,4-dihydro-4-oxo-7-(2,3,5-trimethyl-1-piperazinyl)quinoline-3-carboxylic acid and 1-cyclopropyl-6-fluoro-1,4-dihydro-4-oxo-7-(2,3,5,6-tetramethyl-1-piperazinyl)quinoline-3-carboxylic acid.

The 7-chloro-1-cyclopropyl-6-fluoro-1,4-dihydro-4-oxoquinoline-3-carboxylic acid of the formula VII used as an intermediate can be prepared in accordance with the following reaction diagram.

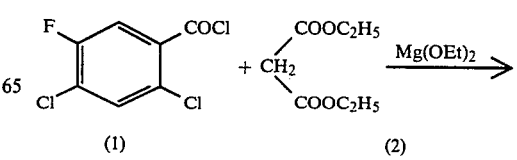

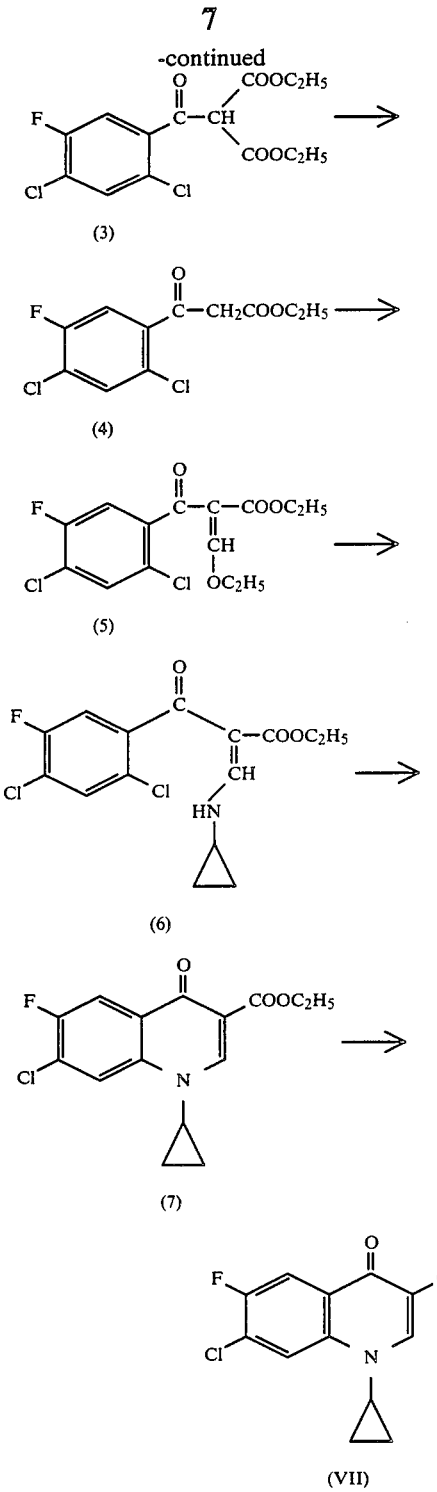

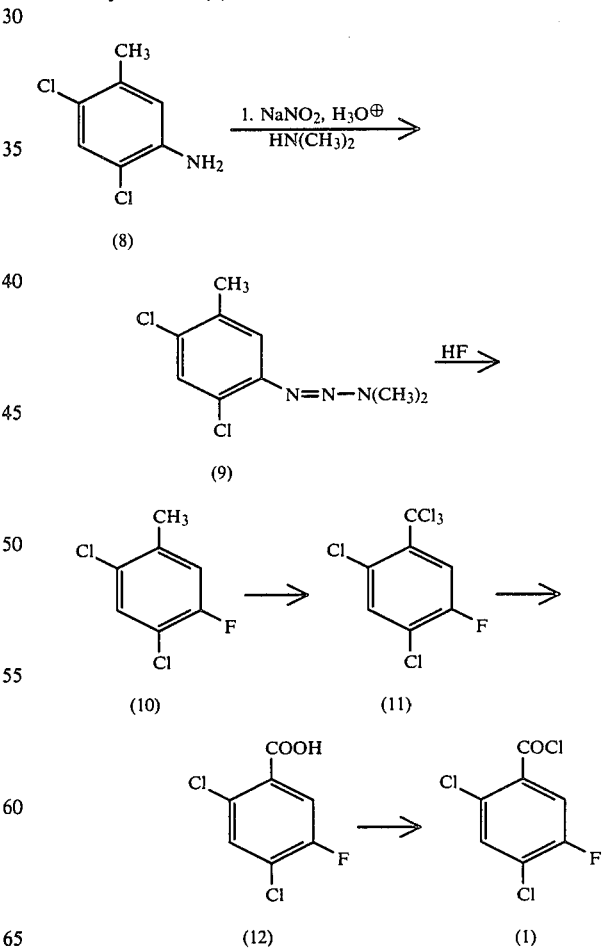

such as, for example, methylene chloride, alcohol, chloroform, cyclohexane or toluene, leads, in a slightly exothermic reaction, to the desired intermediate (6).

The cyclisation reaction (6)→(7) is carried out in the temperature range from about 60° C. to 300° C., preferably 80° C. to 180° C.

Dioxane, dimethyl sulphoxide, N-methylpyrrolidone, sulpholane, hexamethylphosphoric triamide and, preferably, N,N-dimethylformamide can be used as the diluent.

Suitable acid-binding agents for this reaction step are potassium tert.-butanolate, butyllithium, phenyllithium, phenyl magnesium bromide, sodium methylate, sodium hydride and, particularly preferably, potassium carbonate or sodium carbonate. It can be advantageous to employ an excess of 10 mol % of base.

The ester hydrolysis under basic or acid conditions taking place in the last step leads to the 7-chloro-1-cyclopropyl-6-fluoro-1,4-dihydro-4-oxoquinoline-3-carboxylic acid VII.

The 2,4-dichloro-5-fluorobenzoyl chloride (1) used as starting material for this synthetic route, and the corresponding carboxylic acid, as well as the 3-fluoro-4,6-dichlorotoluene (10) required for the preparation of (1) are not yet known.

The diagram below shows the preparation of these precursors or intermediates, starting from 2,4-dichloro-5-methylaniline (8).

According to this, diethyl malonate (2) is acylated with (1) in the presence of magnesium alcoholate with 2,4-dichloro-5-fluorobenzoyl chloride (German Patent Application No. 3,142,856.8) to give the acyl malonate (3) (Organikum, 3rd edition, 1964, page 438).

By partial hydrolysis and decarboxylation of (3) in an aqueous medium with catalytic amounts of sulphuric acid or p-toluenesulphonic acid, the ethyl aroylacetate (4) is obtained in good yield and this is converted with triethyl orthoformate/acetic anhydride into ethyl 2-(2,4-dichloro-5-fluorobenzoyl)-3-ethoxyacrylate (5). Reaction of (5) with cyclopropylamine in a solvent, According to this, 2,4-dichloro-5-methylaniline (8) is diazotised using NaNO₂ and the diazonium salt thereby produced is converted into the triazene (9) with dimethylamine.

The triazene (9) is dissolved in excess anhydrous HF. This cleaves the triazene into 2,4-dichloro-5-methyldiazonium (sic) fluoride and dimethylamine. Without intermediate isolation, this solution is cleaved thermally at 130°–140° C., with elimination of $N_2$, to give 3-fluoro-4,6-dichlorotoluene (10). Yield: 77.7% of theory.

The 3-fluoro-4,6-dichlorotoluene (10) is chlorinated under UV irradiation in the temperature range from 110° to 160° C. to give 2,4-dichloro-5-fluoro-1-trichloromethylbenzene (11).

Hydrolysis of (11) with 95% strength sulphuric acid leads to 2,4-dichloro-5-fluorobenzoic acid (12) which is converted into the carbonyl chloride (1) (boiling point 121°/20 mbar; $n_D^{20}$ 1.5722) with thionyl chloride.

The compounds of the formula (III) which can be used according to the invention are already known or can be obtained by generally known processes. The following may be mentioned as examples: chloroacetaldehyde, chloroacetone, bromoacetone, 1-chlorobutanone, 3-chlorobutanone, 1-chloro-3,3-dimethylbutanone, 1-chloro-2,2-dimethylpropanone, 1-chloro-2-hexanone, 5-bromo-2-pentanone, 2-bromo-3-pentanone, 4-bromo-2-pentanone, phenacyl chloride, 2,4-dihydroxyphenacyl chloride, 3,4-dihydroxyphenacyl chloride, 2-hydroxy-4-methoxyphenacyl chloride, 4-fluorophenacyl chloride, 4-chlorophenacyl chloride 2,4-dichlorophenacyl chloride, 3-bromophenacyl bromide, 4-methylphenacyl bromide, bromoacetaldehyde dimethyl acetal, chloroacetaldehydroxime O-methyl ether, 2-chloromethyl-2-tert.-butyldioxolane and 2-bromomethyldioxolane.

The alkenones of the formula (IV) which can be used according to the invention are already known. The following may be mentioned as examples: acrolein, methyl vinyl ketone, ethyl vinyl ketone, isopropyl vinyl ketone, n-propyl vinyl ketone, n-butyl vinyl ketone, isobutyl vinyl ketone, sec-butyl vinyl ketone, tert.-butyl vinyl ketone, 4-methyl-3-penten-2-one and methyl 2-phenylvinyl ketone.

The hydroxylamines of the formula (VIa) which can be used according to the invention are likewise known. The following may be mentioned as examples: hydroxylamine, methoxyamine, ethoxyamine, n-propoxyamine, tert.-butoxyamine, n-pentyloxyamine, cyclohexyloxyamine, 2-tetrahydropyranyloxyamine, benzyloxyamine, 4-chlorobenzyloxyamine and 2,6-dichlorobenzyloxyamine.

The hydrazine derivatives of the formula (VIb) which can be used according to the invention are already known. The following may be mentioned as examples: methylhydrazine, phenylhydrazine, semicarbazide and thiosemicarbazide.

The reaction of (II) with (III) (method A) is preferably carried out in a diluent, such as dimethyl sulphoxide, N,N-dimethylformamide, hexamethylphosphoric triamide, sulpholane, dioxane, pyridine or an alcohol, at temperatures of 20° C.–180° C., preferably 40° C.–110° C.

The reaction can be carried out under normal pressure, but also under elevated pressure. In general, it is carried out under pressures between about 1 and 10 bar.

All customary inorganic and organic acid-binding agents can be used as the acid-binding agent. These preferably include the alkali metal hydroxides, alkali metal carbonates, pyridine and tert.-amines, such as triethylamine and 1,4-diazabicyclo[2.2.2]octane (DABCO).

In carrying out the process according to the invention, 1 to 4 mols, preferably 1 to 1.5 mols, of compound (III) are employed for 1 mol of compound (II).

The reaction of (II) with (IV) (method B) is preferably carried out in a diluent, such as dioxane, dimethyl sulphoxide, N,N-dimethylformamide, methanol, ethanol, propanol or isopropanol.

The reaction temperatures can be varied within a relatively wide range. In general, the reaction is carried out between about 30° C. and about 150° C., preferably between 50° C. and 110° C.

The reaction can be carried out under normal pressure, but also under elevated pressure. In general, it is carried out under pressures between about 1 and about 100 bar, preferably between 1 and 10 bar.

In carrying out the process according to the invention, 1–5 mols, preferably 1–2 mols, of compound (IV) are employed for 1 mol of compound (II).

The reaction of (V) with (VIa) or (VIb) (method C) is carried out in a diluent, such as water, methanol, ethanol, n-propanol, isopropanol, glycol monomethyl ether, dioxane, N,N-dimethylformamide, dimethyl sulphoxide or in mixtures of these solvents. The catalysts which can be used are inorganic or organic acids, such as hydrochloric acid, sulphuric acid, phosphoric acid, 4-toluenesulphonic acid and salts, such as sodium acetate or potassium acetate. The reaction temperatures can be varied within a relatively wide range. In general, the reaction is carried out between 40° and about 150° C., preferably between 60° and 100° C.

The reaction can be carried out under normal pressure, but also under elevated pressure. In general, it is carried out under pressures between about 1 and about 100 bar, preferably between 1 and 10 bar.

In carrying out the process according to the invention, 1 to 3 mols, preferably 1 to 1.3 mols, of compound (VIa) or (VIb) are employed for 1 mol of compound (V).

The following may be specifically mentioned as new antibacterial active compounds, prepared as described generally above and as described in the working examples: 7-[4-(2-oxopropyl)-1-piperazinyl]-1-cyclopropyl-6-fluoro-1,4-dihydro-4-oxoquinoline-3-carboxylic acid, 7-[4-(3-oxobutyl)-1-piperazinyl]-1-cyclopropyl-6-fluoro-1,4-dihydro-4-oxoquinoline-3-carboxylic acid, 7-[4-(3,3-dimethyl-2-oxobutyl)-1-piperazinyl]-1-cyclopropyl-6-fluoro-1,4-dihydro-4-oxoquinoline-3-carboxylic acid, 7-[4-(1,1-dimethyl-2-oxopropyl)-1-piperazinyl]-1-cyclopropyl-6-fluoro-1,4-dihydro-4-oxoquinoline-3-carboxylic acid, 7-[4-phenacyl-1-piperazinyl]-1-cyclopropyl-6-fluoro-1,4-dihydro-4-oxoquinoline-3-carboxylic acid, 7-[4-(2,4-dihydroxyphenacyl)-1-piperazinyl]-1-cyclopropyl-6-fluoro-1,4-dihydro-4-oxoquinoline-3-carboxylic acid, 7-[4-(3,4-dihydroxyphenacyl)-1-piperazinyl]-1-cyclopropyl-6-fluoro-1,4-dihydro-4-oxoquinoline-3-carboxylic acid, 7-[4-(2-hydroxy-4-methoxyphenacyl)-1-piperazinyl]-1-cyclopropyl-6-fluoro-1,4-dihydro-4-oxoquinoline-3-carboxylic acid, 7-[4-(4-fluorophenacyl)-1-piperazinyl]-1-cyclopropyl-6-fluoro-1,4-dihydro-4-oxoquinoline-3-carboxylic acid, 7-[4-(4-chlorophenacyl)-1-piperazinyl]-1-cyclopropyl-6-fluoro-1,4-dihydro-4-oxoquinoline-3-carboxylic acid, 7-[4-(2-hydroximinoethyl)-1-piperazinyl]-1-cyclopropyl-6-fluoro-1,4-dihydro-4-oxoquinoline-3-carboxylic acid, 7-[4-(2-methoxyiminopropyl)-1-piperazinyl]-1-cyclopropyl-6-fluoro-1,4-dihydro-4-oxoquinoline-3-carboxylic acid, 7-[4-(2-benzyloximinopropyl)-1-piperazinyl]-1-cyclopropyl-6-fluoro-1,4-dihydro-4- oxoquinoline-3-carboxylic acid, 7-{4-[2-(2-tetrahydropyranyloximino)-propyl]-1-piperazinyl}-1-cyclopropyl-6-fluoro-1,4-dihydro-4-oxoquinoline-3-carboxylic acid, 7-[4-(3-oximinobutyl)-1-piperazinyl]-1-cyclopropyl-6-fluoro-1,4-dihydro-4-oxoquinoline-3-carboxylic acid, 7-[4-(2,2-diethoxyethyl)-1-piperazinyl]-1-cyclopropyl-6-fluoro-1,4-dihydro-4-oxoquinoline-3-carboxylic acid, 7-[3-methyl-4-(2-oxopropyl)-1-piperazinyl]-1-cyclopropyl-6-fluoro-1,4-dihydro-4-oxoquinoline-3-carboxylic acid, 7-[3-methyl-4-(3-oxobutyl)-1-piperazinyl]-1-cyclopropyl-6-fluoro-1,4-dihydro-4-oxoquinoline-3-carboxylic acid, 7-[2,5-dimethyl-4-(2-oxopropyl)-1-piperazinyl]-1-cyclopropyl-6-fluoro-1,4-dihydro-4-oxoquinoline-3-carboxylic acid, 7-[2,5-dimethyl-4-(3-oxobutyl)-1-piperazinyl]-1-cyclopropyl-6-fluoro-1,4-dihydro-4-oxoquinoline-3-carboxylic acid, 7-[3,5-dimethyl-4-(2-oxopropyl)-1-piperazinyl]-1-cyclopropyl-6-fluoro-1,4-dihydro-4-oxoquinoline-3-carboxylic acid and 7-[3,5-dimethyl-4-(3-oxobutyl)-1-piperazinyl]-1-cyclopropyl-6-fluoro-1,4-dihydro-4-oxoquinoline-3-carboxylic acid.

The compounds of the formula I obtained according to the invention can optionally be converted into a salt with an organic or inorganic acid. Examples of acids suitable for forming salts are hydrohalic acids, such as hydrochloric acid, hydrobromic acid and hydriodic acid, sulphuric acid, pamoic acid, acetic acid, citric acid, ascorbic acid, lactic acid and benzenesulphonic acid. Alkali metal and alkaline earth metal salts which are preferably suitable are the sodium, potassium, calcium and magnesium salts.

The compounds according to the invention exhibit a broad antibacterial spectrum against Gram-positive and Gram-negative organisms, particularly against enterobacteriaceae; in particular even against those which are resistant to a variety of antibiotics, such as, for example, penicillins, cephalosporins, aminoglycosides, sulphonamides and tetracyclins.

The compounds according to the invention have low toxicity and a potent and broad antimicrobial efficacy. These properties make it possible to use them as chemotherapeutic active compounds in medicine and as substances for preserving inorganic and organic materials, in particular organic materials of all types, for example polymers, lubricants, dyes, fibres, leather, paper and wood, foodstuffs and water.

The compounds according to the invention are active against a very broad spectrum of microorganisms. Using them, Gram-negative and Gram-positive bacteria and bacterioid microorganisms can be controlled and the diseases caused by these pathogens can be prevented, ameliorated and/or cured.

The compounds according to the invention are particularly active against bacteria and bacterioid microorganisms. Thus, they are particularly well suited for the chemotherapy of local and systemic infections caused by these pathogens in medicine.

For example, local and/or systemic diseases caused by the following pathogens or by mixtures of the following pathogens can be treated and/or prevented: Micrococcaceae, such as staphylococci, for example *Staphylococcus aureus, Staph. epidermidis,* (Staph. = Staphylococcus); Lactobacteriaceae, such as streptococci, for example *Streptococcus pyogenes,* α- and β-haemolytic streptococci, non(γ-)haemolytic streptococci, enterocci and *Diplococcus pneumoniae* (pneumococci) (Str. = Streptococcus); Enterobacteriaceae, such as escherichiae bacteria of the coli group: escherichia bacteria, for example *Escherichia coli,* enterobacter bacteria, for example *E. aerogenes, E. cloacae,* klebsiella bacteria, for example *K. pneumoniae,* serratia, for example *Serratia marcescens* (E. = Enterobacter) (K. = Klebsiella), proteae bacteria of the proteus group: proteus, for example *Proteus vulgaris, Pr.morganii, Pr.rettgeri* and *Pr.mirabilis* (Pr. = Proteus); pseudomonadaceae, such as pseudomonas bacteria, for example *Pseudomonas aeruginosa* (PS. = Pseudomonas); bacteroidaceae, such as bacteroides bacteria, for example *Bacteroides fragilis* (B. = Bacteroides); mycoplasma, for example *Mykoplasme pneumoniae.*

The above list of pathogens is merely exemplary and should not by any means be interpreted as restrictive.

The following may be mentioned as examples of illnesses which can be prevented, ameliorated and/or cured by the compounds according to the invention: diseases of the respiratory tract and the pharyngeal cavity: otitis; pharyngitis; pneumonia; peritonitis; pyelonephritis; cystitis; endocarditis; systemic infections; bronchitis; arthritis; local infections and septic diseases.

The present invention includes pharmaceutical preparations which in addition to non-toxic, inert pharmaceutically suitable excipients contain one or more compounds according to the invention or which consist of one or more active compounds according to the invention, and processes for the production of these preparations.

The present invention also includes pharmaceutical preparations in dosage units. This means that the preparations are in the form of individual parts, for example tablets, dragees, capsules, pills, suppositories and ampoules, of which the content of active substance corresponds to a fraction or a multiple of an individual dose. The dosage units can contain, for example, 1, 2, 3 or 4 individual doses or ½, ⅓ or ¼ of an individual dose. An individual dose preferably contains the amount of active compound which is given in one administration and which usually corresponds to a whole, a half or a third or a quarter of a daily dose.

By non-toxic, inert pharmaceutically suitable excipients (i.e. inert pharmaceutical carriers) there are to be understood solid, semi-solid or liquid diluents, fillers and formulation auxiliaries of all kinds.

Tablets, dragees, capsules, pills, granules, suppositories, solutions, suspensions and emulsions, pastes, ointments, gels, creams, lotions, powders and sprays may be mentioned as preferred pharmaceutical preparations.

Tablets, dragees, capsules, pills and granules can contain the active compound or compounds alongside the customary excipients such as (a) fillers and extenders, for example starches, lactose, sucrose, glucose, mannitol and silica, (b) binders, for example carboxymethylcellulose, alginates, gelatine and polyvinylpyrrolidone, (c) humectants, for example glycerine, (d) disintegrating agents, for example agar-agar, calcium carbonate and sodium bicarbonate, (e) solution retarders, for example paraffin, and (f) absorption accelerators, for example quaternary ammonium compounds, (g) wetting agents, for example cetyl alcohol or glycerine monostearate, (h) adsorbents, for example kaolin and bentonite, and (i) lubricants, for example talc, calcium stearate and magnesium stearate and solid polyethylene glycols, or mixtures of the substances listed under (a) to (i).

The tablets, dragees, capsules, pills, and granules can be provided with the customary coatings and shells, optionally containing opacifying agents, and can also be of such composition that they release the active compound or compounds only, or preferentially, in a certain part of the intestinal tract, optionally in a delayed manner, examples of embedding compositions which can be used being polymeric substances and waxes.

The active compound or compounds, optionally together with one or more of the abovementioned excipients, can also be in a micro-encapsulated form.

Suppositories can contain, in addition to the active compound or compounds, the customary water-soluble or water-insoluble excipients, for example polyethylene glycols, fats, for example cacao fat, and higher esters, especially higher aliphatic hydrocarbon esters (for example $C_{14}$-alcohol with $C_{16}$-fatty acid) or mixtures of these substances.

Ointments, pastes, creams and gels can contain the customary excipients in addition to the active compound or compounds, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary excipients in addition to the active compound or compounds, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary excipients in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerine, glycerine-formal, tetrahydrofurfuryl alcohol, polyethylene glycols and fatty acid esters of sorbitan, or mixtures of these substances.

For parenteral administration, the solutions and emulsions can be in a sterile form which is isotonic with blood.

Suspensions can contain the customary excipients in addition to the active compound or compounds, such as liquid diluents, for example water, ethyl alcohol or propylene glycol, suspending agents, for example ethoxylated isostearyl alcohols, polyoxyethylene sorbitol esters and sorbitan esters, microcrystalline cellulose, aluminium metahydroxide, bentonite, agar-agar and tragacanth or mixtures of these substances.

The formulation forms mentioned can also contain dyestuffs, preservatives and additives which have improved odour and flavour, for example peppermint oil and eucalyptus oil, and sweeteners, for example saccharin.

The therapeutically active compounds should preferably be present in the abovementioned pharmaceutical preparations in a concentration of about 0.1 to 99.5, preferably of about 0.5 to 95, % by weight of the total mixture.

The abovementioned pharmaceutical preparations can also contain other pharmaceutical active compounds in addition to the active compounds according to the invention.

The abovementioned pharmaceutical preparations are manufactured in the usual manner according to known methods, for example by mixing the active compound or the active compounds with the excipient or excipients.

The active compounds or the pharmaceutical preparations can be administered locally, orally, parenterally, intraperitoneally and/or rectally, preferably orally or parenterally, such as intravenously or intramuscularly.

In general, it has proved advantageous in medicine to administer the active compound or compounds in total amounts of about 0.5 to about 50, preferably 1 to 30, especially preferably 1–20 mg/kg of body weight, orally or parenterally, every 24 hours, optionally in the form of several individual administrations, in order to achieve the desired results. An individual administration contains the active compound or the active compounds according to the invention preferably in amounts of about 1 to about 250, especially of 3 to 60, mg/kg of body weight every 24 hours. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place. Thus it can suffice in some cases to manage with less than the abovementioned amount of active compound whilst in other cases the abovementioned amount of active compound must be exceeded. The particular required optimum dosage and the type of administration of the active compounds can easily be decided by anyone skilled in the art, on the basis of this expert knowledge.

The new compounds can be administered, for veterinary purposes in the customary concentrations and preparations together with the feed or with the feed preparations or with the drinking water. By this means, an infection by Gram-negative or Gram-positive bacteria can be treated and a promotion of growth and an improvement in the utilisation of the feed can be achieved.

The $R_f$-values indicated in the examples which follow were measured on ready-coated silica gel 60 plates (MERCK/Darmstadt) with methylene chloride/methanol/17% aqueous ammonia (70/8/1) as the mobile phase.

PREPARATION EXAMPLES FOR THE STARTING COMPOUNDS

Example A

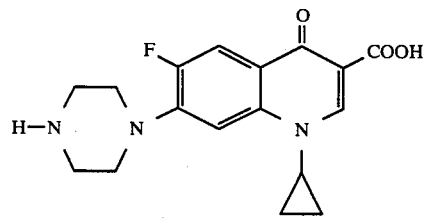

A mixture of 19.7 g of 7-chloro-1-cyclopropyl-6-fluoro-1,4-dihydro-4-oxoquinoline-3-carboxylic acid, 30.1 g of anhydrous piperazine and 100 ml of dimethyl sulphoxide is heated at 135°–140° C. for 2 hours. The solvent is distilled out under high vacuum, and the residue is suspended in $H_2O$, filtered off with suction and washed with water. For further purification, the moist crude product is boiled with 100 ml of water, filtered with suction at room temperature, the solid is washed with H₂O and dried to constant weight over CaCl₂ in a vacuum oven at 100° C. 19.6 g of 1-cyclopropyl-6-fluoro-1,4-dihydro-4-oxo-7-(1-piperazinyl)quinoline-3-carboxylic acid, of decomposition point 255°–257° C., are obtained; $R_F$ value: 0.07.

The 7-chloro-1-cyclopropyl-6-fluoro-1,4-dihydro-4-oxoquinoline-3-carboxylic acid VII used as the starting material is prepared as follows:

24.3 g of magnesium turnings are suspended in 50 ml of anhydrous ethanol. 5 ml of carbon tetrachloride are added and, when the reaction has started up, a mixture of 160 g of diethyl malonate, 100 ml of absolute ethanol and 400 ml of anhydrous ether is added dropwise, vigorous reflux being observed. After the reaction has moderated, the mixture is heated to boiling for 2 hours, then cooled down to −5° C. to −10° C. with dry ice-/acetone and, at this temperature, a solution of 227.5 g of 2,4-dichloro-5-fluorobenzoyl chloride (1) in 100 ml of absolute ether is slowly added dropwise. The mixture is stirred at 0° C. for 1 hour, allowed to reach room temperature overnight and, while cooling in ice, a mixture of 400 ml of ice-water and 25 ml of concentrated sulphuric acid is allowed to run in. The phases are separated and the aqueous phase is extracted twice more with ether. The combined ether solutions are washed with saturated NaCl solution, dried with Na₂SO₄ and the solvent is removed in vacuo. 349.5 g of diethyl 2,4-dichloro-5-fluorobenzoylmalonate (3) are obtained as a crude product.

0.15 g of p-toluenesulphonic acid is added to an emulsion of 34.9 g of crude diethyl 2,4-dichloro-5-fluorobenzoylmalonate (3) in 50 ml of water. The mixture is heated to boiling, with thorough stirring, for 3 hours, the cooled emulsion is extracted several times with methylene chloride, the combined CH₂Cl₂ solutions are washed once with saturated NaCl solution, dried with Na₂SO₄ and the solvent is distilled out in vacuo. Fractionation of the residue under high vacuum provides 21.8 g of ethyl 2,4-dichloro-5-fluorobenzoylacetate (4) of boiling point 127°–142° C./0.09 mbar.

A mixture of 21.1 g of ethyl 2,4-dichloro-5-fluorobenzoylacetate (4), 16.65 g of ethyl orthoformate and 18.55 g of acetic anhydride is heated at 150° C. for 2 hours. The volatile components are then distilled out under waterpump vacuum and finally under high vacuum at a bath temperature of 120° C. 25.2 g of crude ethyl 2-(2,4-dichloro-5-benzoyl(sic))-3-ethoxyacrylate (5) remain behind. This is pure enough for the subsequent reactions.

4.3 g of cyclopropylamine are added dropwise, with cooling in ice and stirring, to a solution of 24.9 g of ethyl 2-(2,4-dichloro-5-fluorobenzoyl)-3-ethoxyacrylate (5) in 80 ml of ethanol. When the exothermic reaction has moderated, the mixture is stirred at room temperature for a further 1 hour, the solvent is removed in vacuo and the residue is recrystallised from cyclohexane/petroleum ether. 22.9 g of ethyl 2-(2,4-dichloro-5-fluorobenzoyl)-3-cyclopropylaminoacrylate (6) of melting point 89°–90° C. are obtained.

3.44 g of 80% sodium hydride are added in portions, with cooling in ice and stirring, to a solution of 31.9 g of ethyl 2-(2,4-dichloro-5-fluorobenzoyl)-3-cyclopropylaminoacrylate (6) in 100 ml of anhydrous dioxane. The mixture is then stirred at room temperature for 30 minutes and under reflux for 2 hours and the dioxane is removed in vacuo. The residue (40.3 g) is suspended in 150 ml of water, 6.65 g of potassium hydroxide are added and the mixture is refluxed for 1.5 h. The warm solution is filtered and washed with H₂O. The solution is then acidified to pH 1 to 2 with half-concentrated hydrochloric acid, cooling in ice, the precipitate is filtered off with suction, washed with water and dried in vacuo at 100° C. In this manner, 27.7 g of 7-chloro-1-cyclopropyl-6-fluoro-1,4-dihydro-4-oxoquinoline-3-carboxylic acid VII, of melting point 234°–237° C., are obtained.

Example B

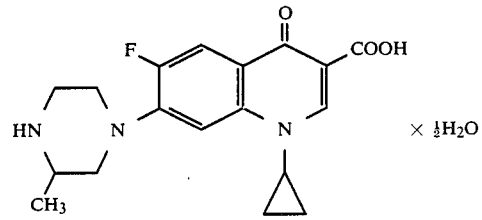

A mixture of 2.8 g (0.01 mol) of 7-chloro-1-cyclopropyl-6-fluoro-1,4-dihydro-4-oxoquinoline-3-carboxylic acid and 5.1 g (0.051 mol) of 2-methylpiperazine in 6 ml of dimethyl sulphoxide is heated at 140° C. for 2 hours. The solvent is then distilled out under high vacuum, 6 ml of hot water are added to the residue and the mixture is kept at 95° C. for 1 hour. It is then cooled with ice, the precipitate which has separated out is filtered off with suction, washed with a little water and dissolved in a mixture of 0.8 ml of acetic acid and 10 ml of water at 90° to 100° C. The filtrate is adjusted to pH 8 with potassium hydroxide solution (0.75 g of KOH in 0.7 ml of water) and the precipitate which has separated out is recrystallised from methanol. 1.8 g (52% of theory) of 1-cyclopropyl-6-fluoro-1,4-dihydro-4-oxo-7-(3-methyl-1-piperazinyl)quinoline-3-carboxylic acid semihydrate, with a decomposition point of 230°–232° C., is obtained. $R_F$ value: 0.11.

The following examples illustrate the preparation of the compounds according to the invention:

Example 1

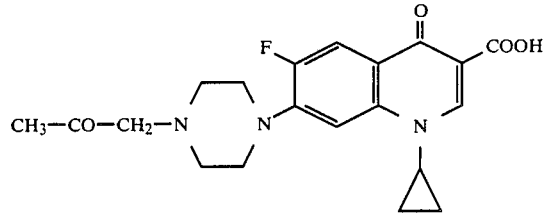

A mixture of 23.2 g (0.07 mol) of 1-cyclopropyl-6-fluoro-1,4-dihydro-4-oxo-7-(1-piperazinyl)quinoline-3-carboxylic acid and 9.8 g of chloroacetone in 350 ml of dimethylformamide and 14.7 g of triethylamine is heated at 80° C. for 3 hours. The mixture is evaporated under high vacuum, the residue is thoroughly stirred with 140 ml of water and the undissolved solid is recrystallised from glycol monomethyl ether. Yield: 17 g (62.8% of theory) of 1-cyclopropyl-6-fluoro-1,4-dihydro-4-oxo-7-[4-(2-oxopropyl)-1-piperazinyl]quinoline-3-carboxylic acid with a decomposition point of 220°–225° C., $R_f$ value=0.15.

In analogy to Example 1, the following compounds are prepared:

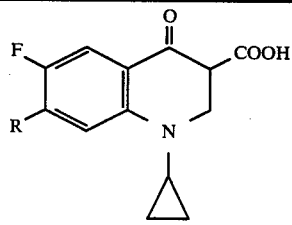

| Example | R | Melting point | $R_f$ value |
|---|---|---|---|
| 2 | (CH₃)₃C—CO—CH₂—N⌒N— | 207–210° C. | 0.22 |
| 3 | CH₃—CO—C(CH₃)₂—N⌒N— | 268–271° C. | 0.29 |
| 4 | Ph—CO—CH₂—N⌒N— | 198–202° C. | 0.32 |
| 5 | HO—C₆H₃(OH)—CO—CH₂—N⌒N— | 150–154° C. | 0.16 |
| 6 | HO—C₆H₃(OH)—CO—CH₂—N⌒N— | 210–215° C. | 0.08 |
| 7 | CH₃O—C₆H₃(OH)—CO—CH₂—N⌒N— | 224–227° C. | 0.32 |
| 8 | F—C₆H₄—CO—CH₂—N⌒N— | 168–171° C. (decomposition) | 0.33 |
| 9 | Cl—C₆H₄—CO—CH₂—N⌒N— | 197–199° C. (decomposition) | 0.32 |

Example 10

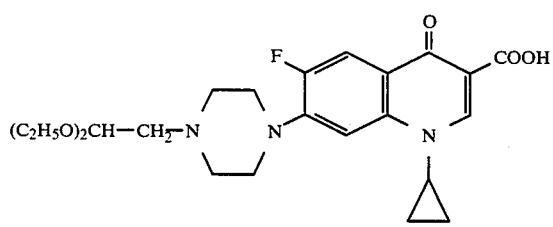

A mixture of 3.3 g (0.01 mol) of 1-cyclopropyl-6-fluoro-1,4-dihydro-4-oxo-7-(1-piperazinyl)quinoline-3-carboxylic acid, 3.85 g (0.02 mol) of bromoacetaldehyde diethyl acetal, 2.1 g of triethylamine and 3.35 g of potassium iodide is heated at 90° C. for 11 hours. The solution is evaporated under high vacuum, the residue is thoroughly stirred with 20 ml of methanol and the precipitate which has separated out is washed several times with water and extracted by boiling with methanol. Yield: 1.3 g (29%) of 1-cyclopropyl-7-[4-(2,2-diethoxyethyl)-1-piperazinyl]-6-fluoro-1,4-dihydro-4-oxoquinoline-3-carboxylic acid with a decomposition point of 208°–212° C.; $R_F$ value: 0.40.

Example 11

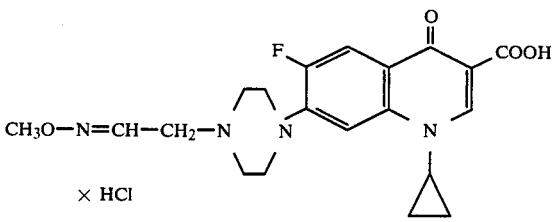

A mixture of 3.3 g (0.01 mol) of 1-cyclopropyl-6-fluoro-1,4-dihydro-4-oxo-7-(1-piperazinyl)quinoline-3-carboxylic acid, 1.6 g of chloroacetaldehyde oxime O-methyl ether and 2.1 g of triethylamine is stirred at 80° C. for 3 hours. The mixture is then evaporated under high vacuum, 30 ml of water are added and the pH is adjusted to 2 with 2N HCl. The precipitate is filtered off with suction, washed with water and methanol and dried under high vacuum. Yield: 1.9 g (43% of theory) of 1-cyclopropyl-6-fluoro-1,4-dihydro-7-[4-(2-methoximinoethyl)-1-piperazinyl]-4-oxoquinoline-3-carboxylic acid hydrochloride with a decomposition point of 215°–221° C., $R_F$ value: 0.29.

NMR (d₆-DMSO): 3.87 and 3.88 (2 singlets for the CH₃O groups of the syn and anti forms).

Mass spectrum: m/e 402, 371, 331, 289, 287, 245 (100%) 229, 70, 56, 44, 32, 31, 27.

Example 12

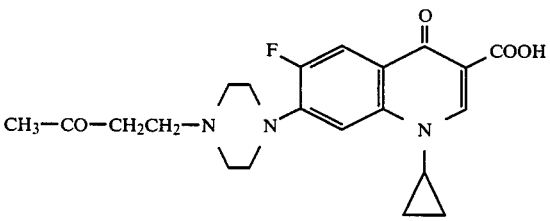

3.31 g (0.01 mol) of 1-cyclopropyl-6-fluoro-1,4-dihydro-4-oxo-7-(1-piperazinyl)quinoline-3-carboxylic acid and 3.9 g of methyl vinyl ketone in 50 ml of ethanol are heated under reflux for 2 hours. The solid is filtered off with suction, washed with methanol and 2.5 g (62.3% of theory) of 1-cyclopropyl-6-fluoro-1,4-dihydro-4-oxo-7-[4-(3-oxobutyl)-1-piperazinyl]quinoline-3-carboxylic acid, with a decomposition point of 185°–187° C., are obtained; $R_f$ value: 0.14.

Example 13

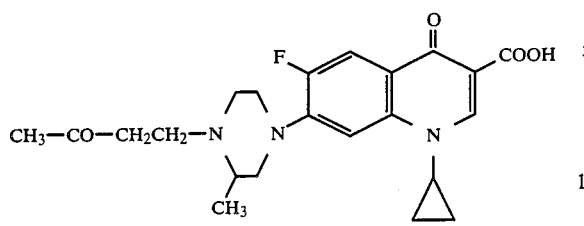

In analogy to Example 12 and with the stirring material from Example B, 1-cyclopropyl-6-fluoro-1,4-dihydro-7-[3-methyl-4-(3-oxobutyl)-1-piperazinyl]-4-oxoquinoline-3-carboxylic acid (87% of theory) is obtained with a decomposition point of 176°–178° C.; $R_f$ value: 0.39.

Example 14

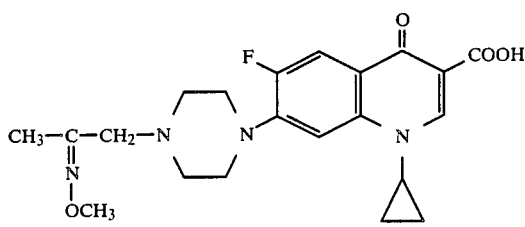

0.5 ml of concentrated hydrochloric acid is added to a mixture of 3.87 g (0.01 mol) of 1-cyclopropyl-6-fluoro-1,4-dihydro-4-oxo-7-[4-(2-oxopropyl)-1-piperazinyl]-quinoline-3-carboxylic acid and 835 mg (0.01 mol) of methoxyamine hydrochloride in 120 ml of ethanol and the mixture is heated under reflux for 3 hours. The hot solution is thoroughly stirred with a little "Tonsil" (fuller's earth) and filtered. The crystals which separate out after cooling down are filtered off with suction, washed with ether and dried. Yield: 2.1 g (46% of theory) of 1-cyclopropyl-6-fluoro-1,4-dihydro-7-[4-(2-methoximino-propyl)-1-piperazinyl]-4-oxoquinoline-3-carboxylic acid with a decomposition point of 215°–217° C.; $R_f$ value: 0.37.

In analogy to Example 14, the following compounds are obtained:

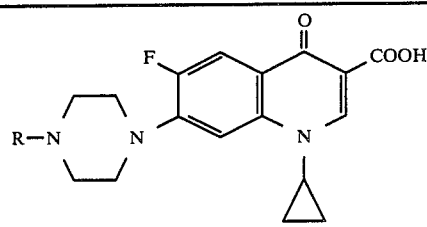

| Example | R | Melting point | $R_f$ value |
|---|---|---|---|
| 15 | CH₃—C(=N—OCH₃)—CH₂—CH₂ × HCl | 315–320° C. (decomposition) | 0.39 |
| 16 | CH₃—C(=N—O—CH₂—C₆H₅)—CH₂ | 184–188° C. (decomposition) | 0.40 |
| 17 | CH₃—C(=N—O—tetrahydropyranyl)—CH₂ | 105–110° C. (decomposition)* | 0.39 |
| 18 | CH₃—C(=N—NH—CO—NH₂)—CH₂ × HCl × 2H₂O | 217–219° C. (decomposition) | 0.1 |
| 19 | CH₃—C(=N—NH—CS—NH₂)—CH₂ × HCl × H₂O | 219–221° C. (decomposition) | 0.24 |

*solidified foam; the tetrahydropyranyl radical has been partially split off.

In the table below, the minimum inhibitory concentrations (MIC) with a variety of bacteria for some of the compounds according to the invention are given.

| | Minimum inhibitory concentrations in mcg/ml in the agar dilution test; Denley multipoint inoculation procedure | | | | | |
|---|---|---|---|---|---|---|
| Strain | Example 4 | Example 1 | Example 5 | Example 8 | Example 12 | Example 9 |
| E. coli Neumann | 0.03 | 0.06 | | 0.015 | ≦0.015 | 0.03 |
| E. coli A 261 | ≦0.015 | ≦0.015 | | ≦0.015 | ≦0.015 | ≦0.015 |
| Klebsiella 8085 | 0.125 | 0.06 | | 0.03 | ≦0.015 | 0.125 |
| Klebsiella 6179 | 0.5 | 2 | | 0.25 | 0.25 | 1 |
| Klebsiella 57 USA | 0.06 | 1 | | 0.03 | 0.06 | 0.5 |
| Proteus morganii 932 | ≦0.015 | 0.06 | | ≦0.015 | ≦0.015 | 0.03 |
| Providencia 12052 | 128 | 128 | | 64 | 32 | >128 |
| Staphylococcus Fk 422 | 2 | 0.25 | 0.25 | 1 | 0.5 | 2 |
| 1746 | 1 | 0.25 | 0.25 | 1 | 0.5 | 2 |
| 133 | 2 | 0.25 | 0.25 | 1 | 0.5 | 2 |

What is claimed is:

1. A 1-cyclopropyl-6-fluoro-1,4-dihydro-4-oxo-7-[4-(oxoalkyl)-1-piperazinyl]quinoline-3-carboxylic acid of the formula (I)

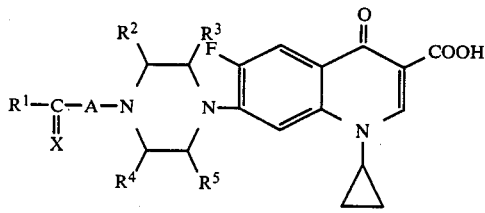

in which
R¹ denotes hydrogen, straight-chain or branched alkyl having 1 to 4 carbon atoms and phenyl which is optionally substituted 1–3 times by trifluoromethyl, methyl, ethyl, fluorine, chlorine, bromine, phenyl, hydroxyl or alkoxy having 1–4 carbon atoms, R², R³, R⁴ and R⁵ can be identical or different and denote hydrogen, methyl, ethyl, n- or i-propyl, X denotes O, N—O—R', N—NH—R'' and (OR''')₂, in which R' represents hydrogen, straight-chain or branched alkyl having 1 to 6 carbon atoms, cycloalkyl having 5 to 6 carbon atoms, benzyl, chlorobenzyl or tetrahydropyranyl, R'' represents methyl, phenyl, carbamoyl or thiocarbamoyl and R''' represents methyl and ethyl or (OR''')₂ represents

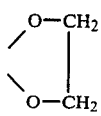

and

A denotes an alkylene group having 1–4 carbon atoms, which is optionally substituted by alkyl having 1–4 carbon atoms or phenyl, and their pharmaceutically utilisable acid addition, alkali metal and alkaline earth metal salts and hydrates.

2. A 1-cyclopropyl-6-fluoro-1,4-dihydro-4-oxo-7-[4-(oxoalkyl)-1-piperazinyl]quinoline-3-carboxylic acid of claim 1 of the formula (I)

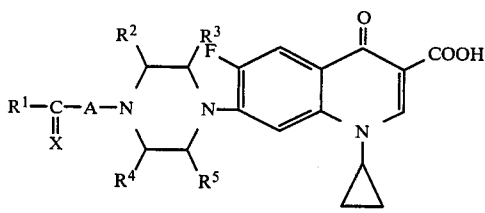

in which
R¹ denotes hydrogen, straight-chain or branched alkyl having 1–3 carbon atoms or phenyl which is optionally substituted 1–3 times by trifluoromethyl, methyl, ethyl, fluorine, chlorine, bromine, phenyl, hydroxyl or alkoxy having 1–4 carbon atoms, R², R³, R⁴ and R⁵ denote hydrogen, methyl or ethyl, X denotes O, N—O—R', N—NH—R'' or (OR''')₂, in which R' denotes hydrogen, alkyl having 1–4 carbon atoms, benzyl or tetrahydropyranyl, R'' denotes carbamoyl or thiocarbamoyl, R''' denotes methyl or ethyl and A denotes alkylene having 1–3 carbon atoms, and their pharmaceutically utilisable acid addition, alkali metal and alkaline earth metal salts and hydrates.

3. A 1-cyclopropyl-6-fluoro-1,4-dihydro-4-oxo-7-[4-(oxoalkyl)-1-piperazinyl]quinoline-3-carboxylic acid of claim 1 of the formula (I)

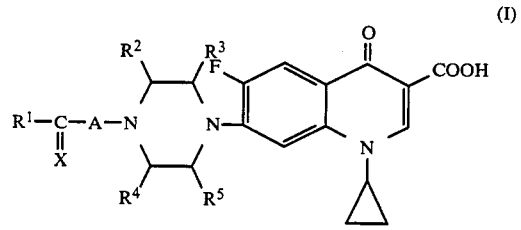

in which
R¹ denotes hydrogen, alkyl having 1–2 carbon atoms or phenyl which is optionally substituted 1–2 times by trifluoromethyl, methyl, fluorine, chlorine, hydroxyl or alkoxy having 1–2 carbon atoms, R² denotes hydrogen, methyl or ethyl, R³ denotes hydrogen, R⁴ denotes hydrogen, ethyl or methyl, R⁵ denotes hydrogen or methyl, X denotes O, N—O—R', N—NH—R'' or (OR''')₂, in which R' denotes hydrogen, alkyl having 1–2 carbon atoms, benzyl or tetrahydropyranyl, R'' denotes carbamoyl or thiocarbamoyl, R''' denotes methyl or ethyl and A denotes alkylene having 1–2 carbon atoms, and their pharmaceutically utilisable acid addition, alkali metal and alkaline earth metal salts and hydrates.

4. A compound of claim 1 which is 1-cyclopropyl-6-fluoro-1,4-dihydro-4-oxo-7-[4-(2-oxopropyl)-1-piperazinyl]quinoline-3-carboxylic acid or a pharmaceutically utilisable acid addition salt thereof.

5. A compound of claim 1 which is 1-cyclopropyl-6-fluoro-1,4-dihydro-4-oxo-7-[4-(4-fluorophenacyl)-1-piperazinyl]quinoline-3-carboxylic acid or a pharmaceutically utilisable acid addition salt thereof.

6. A compound of claim 1 which is 1-cyclopropyl-6-fluoro-1,4-dihydro-4-oxo-7-[4-(2-methoximinobutyl)-1-piperazinyl]quinoline-3-carboxylic acid or a pharmaceutically utilisable acid addition salt thereof.

7. A compound of claim 1 which is 1-cyclopropyl-6-fluoro-1,4-dihydro-4-oxo-7-[4-(3-oxobutyl)-1-piperazinyl]quinoline-3-carboxylic acid or a pharmaceutically utilisable acid addition salt thereof.

8. A compound of claim 1 which is 1-cyclopropyl-6-fluoro-1,4-dihydro-4-oxo-7-[3-methyl-4-(3-oxobutyl)-1-piperazinyl]quinoline-3-carboxylic acid or a pharmaceutically utilisable acid addition salt thereof.

9. A 1-cyclopropyl-6-fluoro-1,4-dihydro-4-oxo-7-[4-(oxoalkyl)-1-piperazinyl]quinoline-3-carboxylic acid of the formula (I)

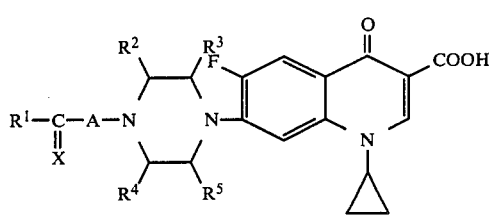

in which

R[1] denotes hydrogen, straight-chain or branched alkyl having 1 to 4 carbon atoms and phenyl which is optionally substituted 1-3 times by trifluoromethyl, methyl, ethyl, fluorine, chlorine, bromine, phenyl, hydroxyl or alkoxy having 1-4 carbon atoms, R[2], R[3], R[4] and R[5] can be identical or different and denote hydrogen, methyl, ethyl, n- or i-propyl, X denotes O, N—O—R', N—NH—R'' and (OR''')$_2$, in which R' represents hydrogen, straight-chain or branched alkyl having 1 to 6 carbon atoms, cycloalkyl having 5 to 6 carbon atoms, benzyl, chlorobenzyl or tetrahydropyranyl, R'' represents methyl, phenyl, carbamoyl or thiocarbamoyl and R''' represents methyl and ethyl or (OR''')$_2$ represents

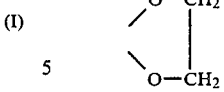

and

A denotes an alkylene chain having 1 to 4 carbon atoms, which is optionally substituted by alkyl having 1-4 carbon atoms or phenyl, and their pharmaceutically utilisable acid addition, alkali metal and alkaline earth metal salts and hydrates for the treatment of bacterial diseases.

10. A pharmaceutical composition containing as active ingredient an antibacterially effective amount of a compound of claim 1 together with an inert pharmaceutical carrier.

11. A pharmaceutical composition of claim 10 in the form of a sterile or physiologically isotonic aqueous solution.

12. A composition of claim 10 containing from 0.5 to 95% by weight of the said active ingredient.

13. A medicament in dosage unit form containing an antibacterially effective amount of a compound according to claim 1 and an inert pharmaceutical carrier.

14. A medicament of claim 13 in the form of tablets, pills, dragees, capsules, ampoules or suppositories.

15. A method of combatting bacterial infection in a warm-blooded animal which comprises administering to said animal an antibacterially effective amount of an active compound of claim 1 either alone or in admixture with an inert pharmaceutical carrier or in the form of a medicament.

16. A method of claim 16 wherein the active compound is administered in an amount of about 1 to about 250 mg/kg of body weight per day.

17. A feedstuff additive composition comprising an active compound of claim 1 together with an animal feed or drinking water.

* * * * *